US012582207B2

(12) United States Patent
Ball

(10) Patent No.: US 12,582,207 B2
(45) Date of Patent: Mar. 24, 2026

(54) CONTACT LENS CLEANING CASE

(71) Applicant: Sherri Ball, Reseda, CA (US)

(72) Inventor: Sherri Ball, Reseda, CA (US)

( * ) Notice: Subject to any disclaimer, the term of this patent is extended or adjusted under 35 U.S.C. 154(b) by 267 days.

(21) Appl. No.: 18/367,830

(22) Filed: Sep. 13, 2023

(65) Prior Publication Data

US 2025/0082080 A1     Mar. 13, 2025

(51) Int. Cl.
| | |
|---|---|
| *A45C 11/00* | (2006.01) |
| *A61L 12/08* | (2006.01) |
| *B65D 41/04* | (2006.01) |
| *B65D 81/26* | (2006.01) |
| *B65D 85/00* | (2006.01) |

(52) U.S. Cl.
CPC .......... *A45C 11/005* (2013.01); *A61L 12/086* (2013.01); *B65D 41/04* (2013.01); *B65D 81/261* (2013.01); *B65D 85/54* (2013.01); *B65D 2585/545* (2013.01)

(58) Field of Classification Search
None
See application file for complete search history.

(56) References Cited

U.S. PATENT DOCUMENTS

| | | | |
|---|---|---|---|
| 4,721,124 A | | 1/1988 | Tuerkheimer |
| 5,234,010 A | * | 8/1993 | Grondin ............... A45C 11/005 |
| | | | 134/158 |
| D498,590 S | | 11/2004 | Borovsky |
| 6,868,963 B2 | | 3/2005 | Borovsky |
| 7,540,376 B2 | | 6/2009 | Mahieu |
| 7,699,161 B2 | | 4/2010 | Tokarski |
| 9,439,990 B2 | | 9/2016 | Powell |
| 2012/0085662 A1 | | 4/2012 | Mori |

FOREIGN PATENT DOCUMENTS

GB          2214654          6/1989

* cited by examiner

*Primary Examiner* — Cristi J Tate-Sims

(57) ABSTRACT

A contact lens cleaning apparatus for cleaning contact lenses outside of a user's hands includes a housing containing a pair of motors. A pair of fluid permeable containers are positioned outside of the housing and are attached to respective motors via shafts. The motors are operable to rotate the shafts, thus rotating the fluid permeable containers.

10 Claims, 9 Drawing Sheets

CONTACT LENS CLEANING CASE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to contact lens cleaning apparatuses and more particularly pertains to a new contact lens cleaning apparatus for cleaning contact lenses outside of a user's hands.

(2) Description of Related Art Including Information Disclosed Under 37 CFR 1.97 and 1.98

The prior art describes myriad contact lens cleaning apparatuses. However, there prior art fails to disclose such an apparatus which allows for rinsing of the contact lenses in fluid permeable containers while the containers move to distribute contact solution being poured over the contact lenses.

BRIEF SUMMARY OF THE INVENTION

An embodiment of the disclosure meets the needs presented above by generally comprising a housing and a pair of motors mounted in the housing. Each one of a pair of shafts is operatively coupled to an associated motor of the pair of motors. Each shaft of the pair of shafts extends away from the associated motor out of the housing and is rotatable about a central axis of the shaft. Each one of a pair of containers is mounted on a distal end of an associated shaft of the pair of shafts with respect to the associated motor. Each container defines an interior space in the container with a size such that the container is configured to contain an associated one of a pair of contact lenses. The containers are urged to rotate by the shafts when the shafts rotate. Each container is fluid permeable.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
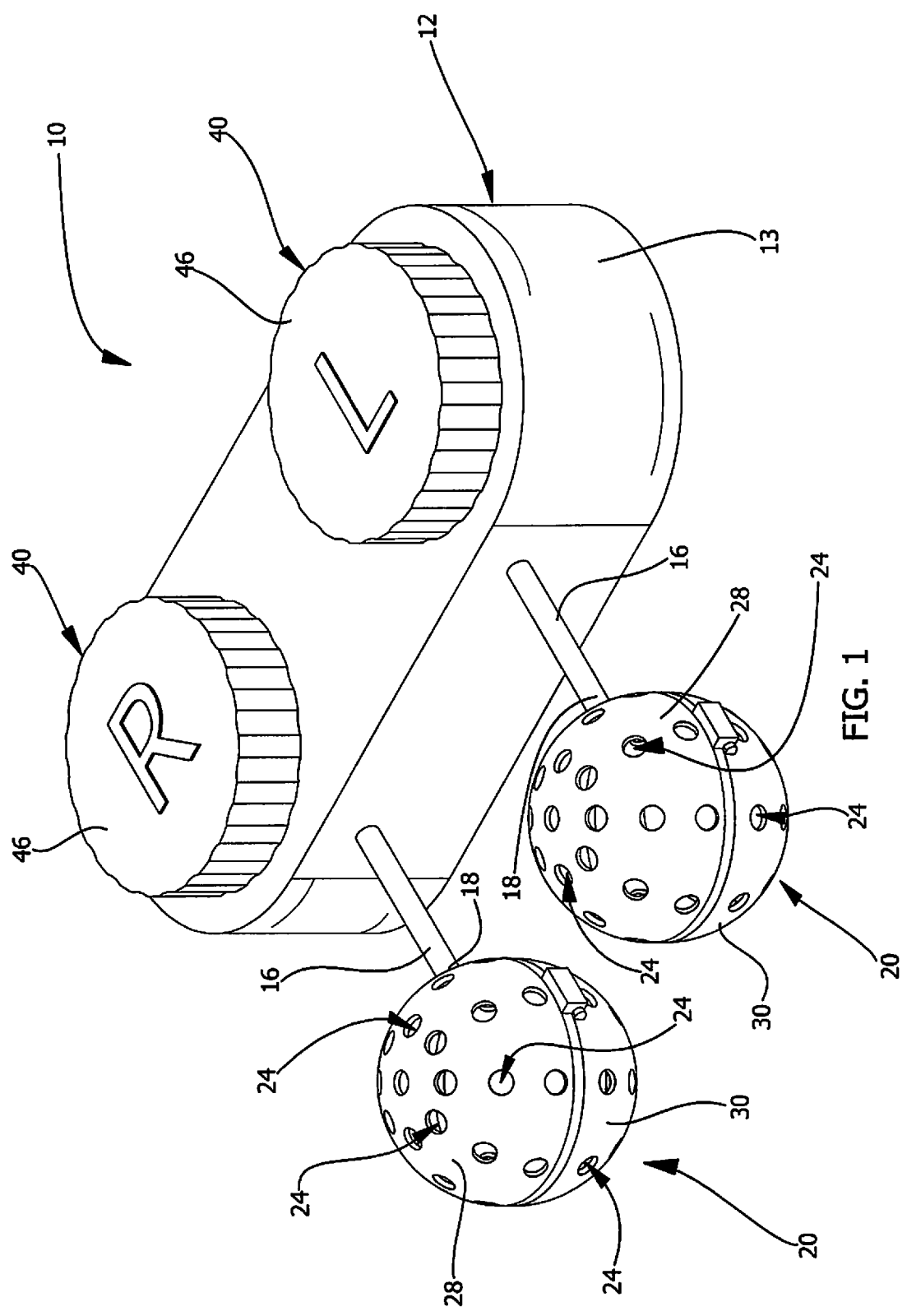
FIG. 1 is a top front side perspective view of a contact lens cleaning apparatus according to an embodiment of the disclosure.
Figure 2:
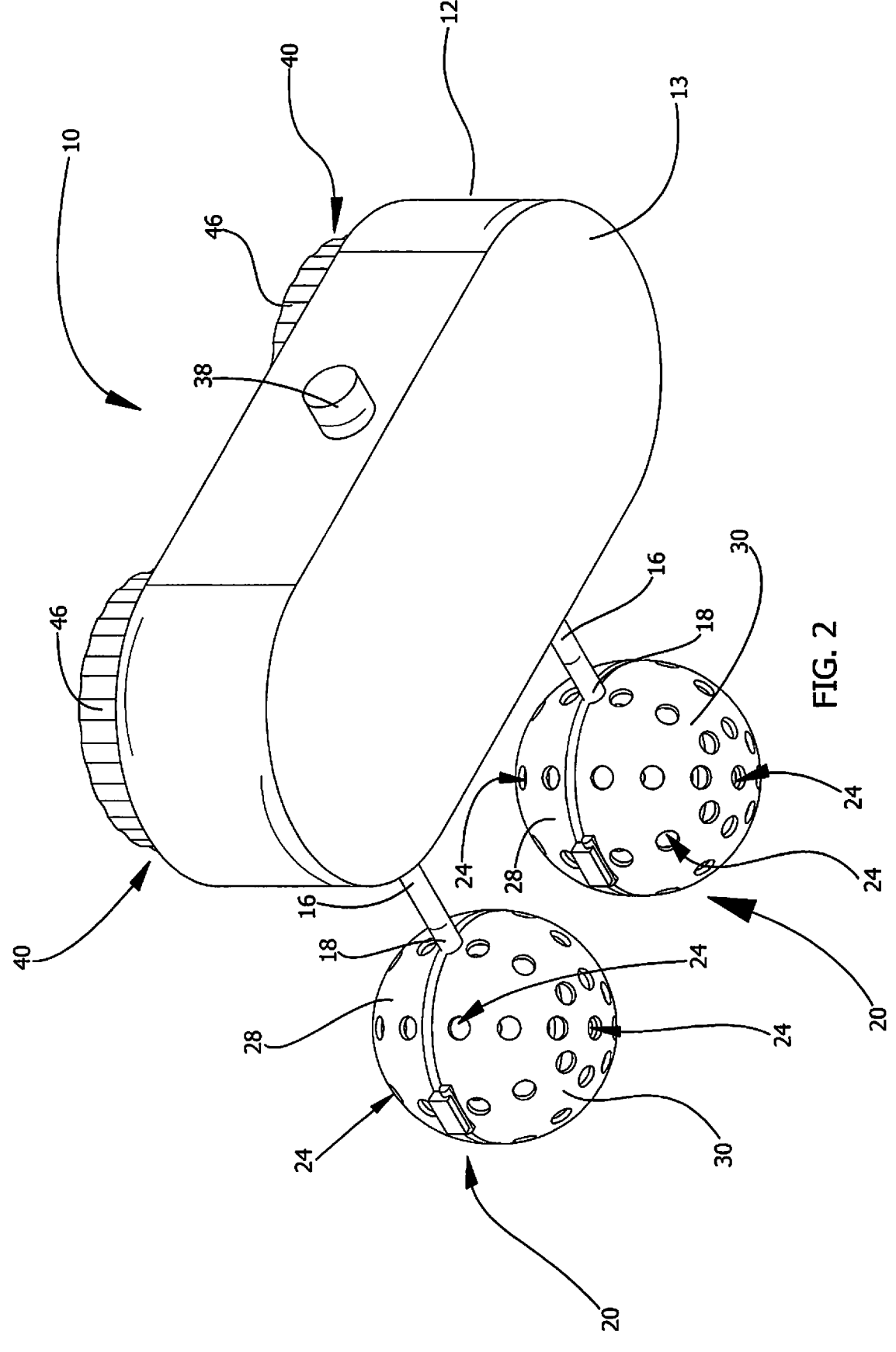
FIG. 2 is a bottom rear side perspective view of an embodiment of the disclosure.
Figure 3:
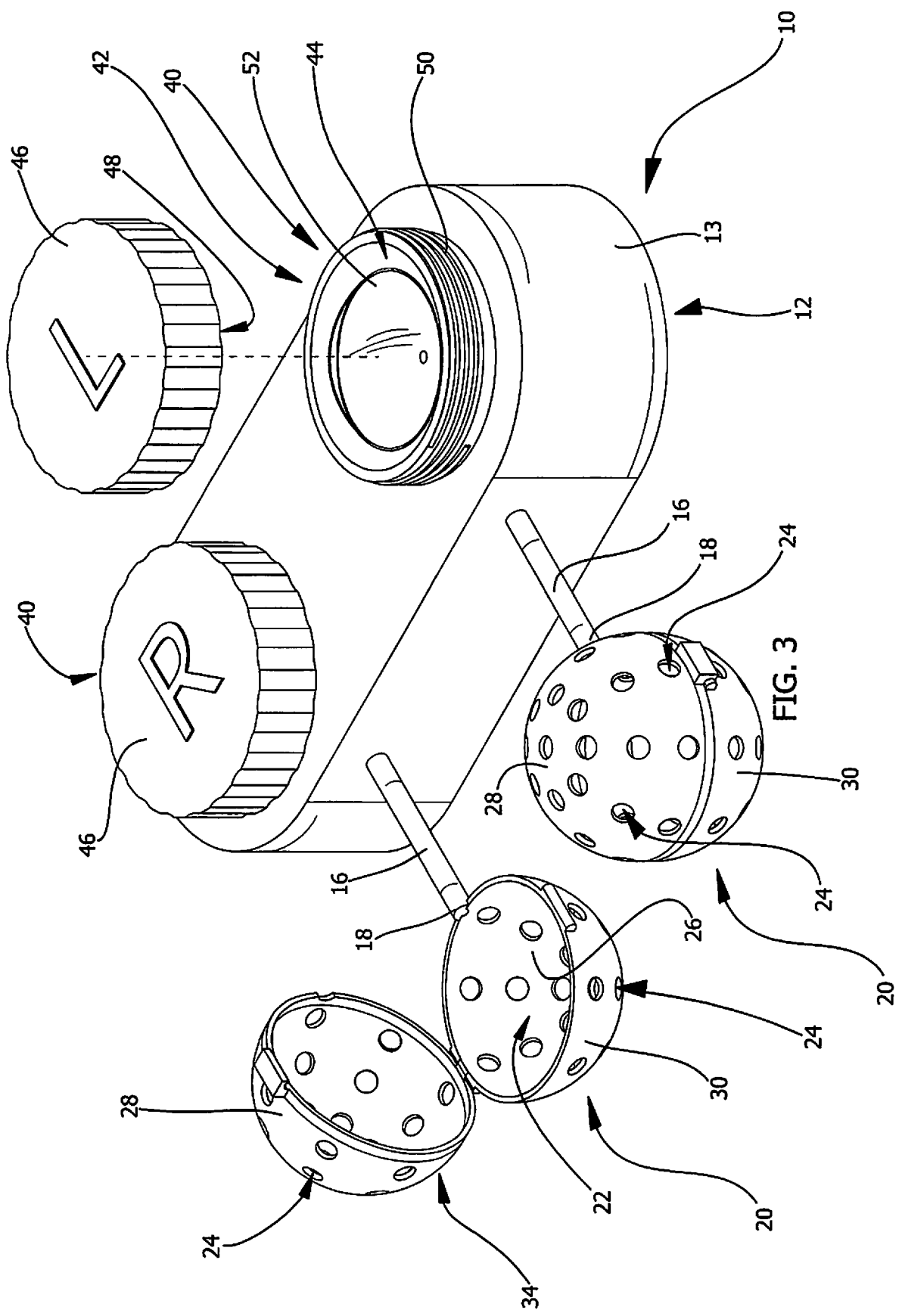
FIG. 3 is a top front side perspective view of an embodiment of the disclosure with a cap being removed from a storage vessel and a container in an open configuration.
Figure 4:
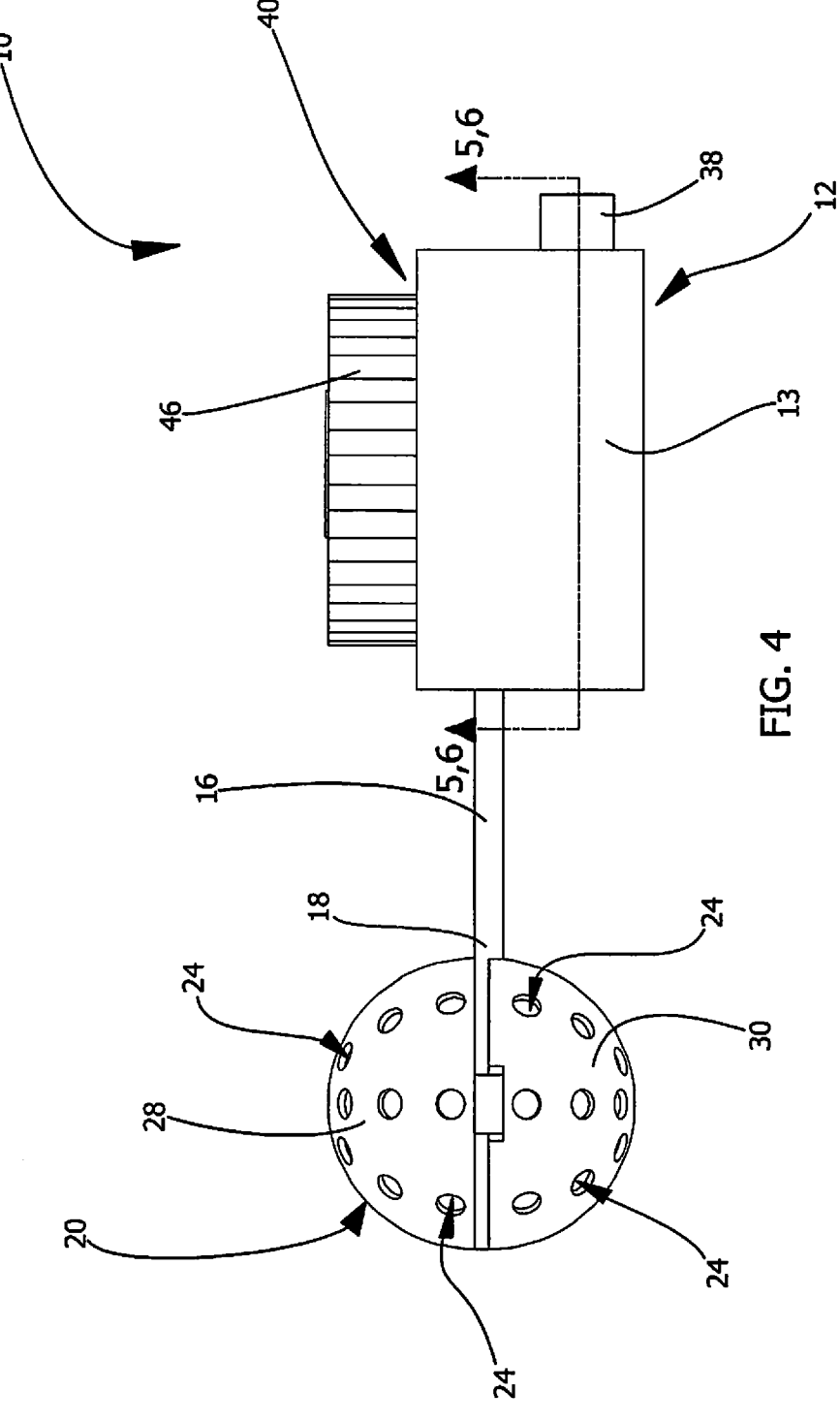
FIG. 4 is a side view of an embodiment of the disclosure.
Figure 5:
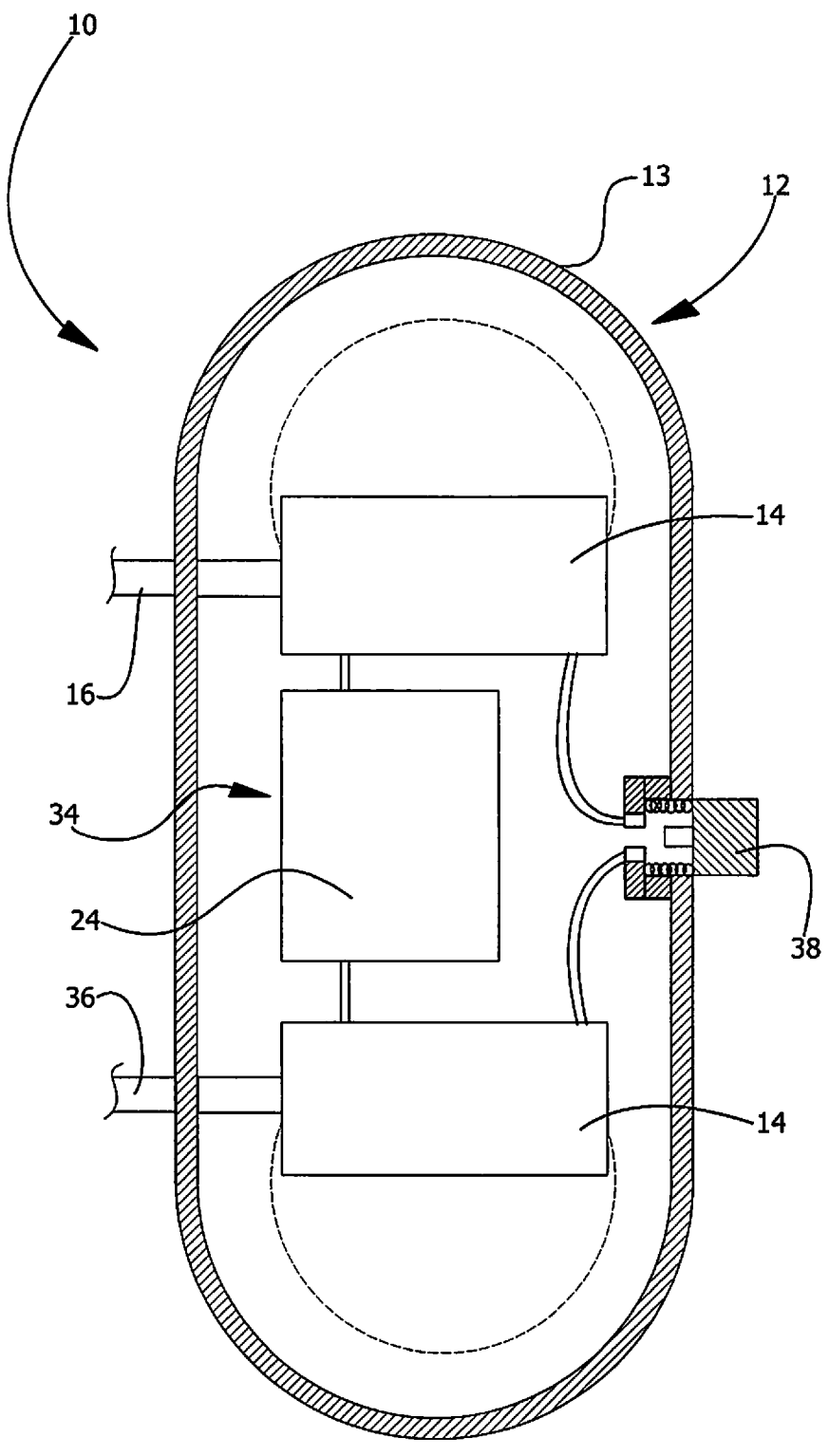
FIG. 5 is a cross section view of an embodiment of the disclosure taken from Arrows 5-5 in FIG. 4.
Figure 6:
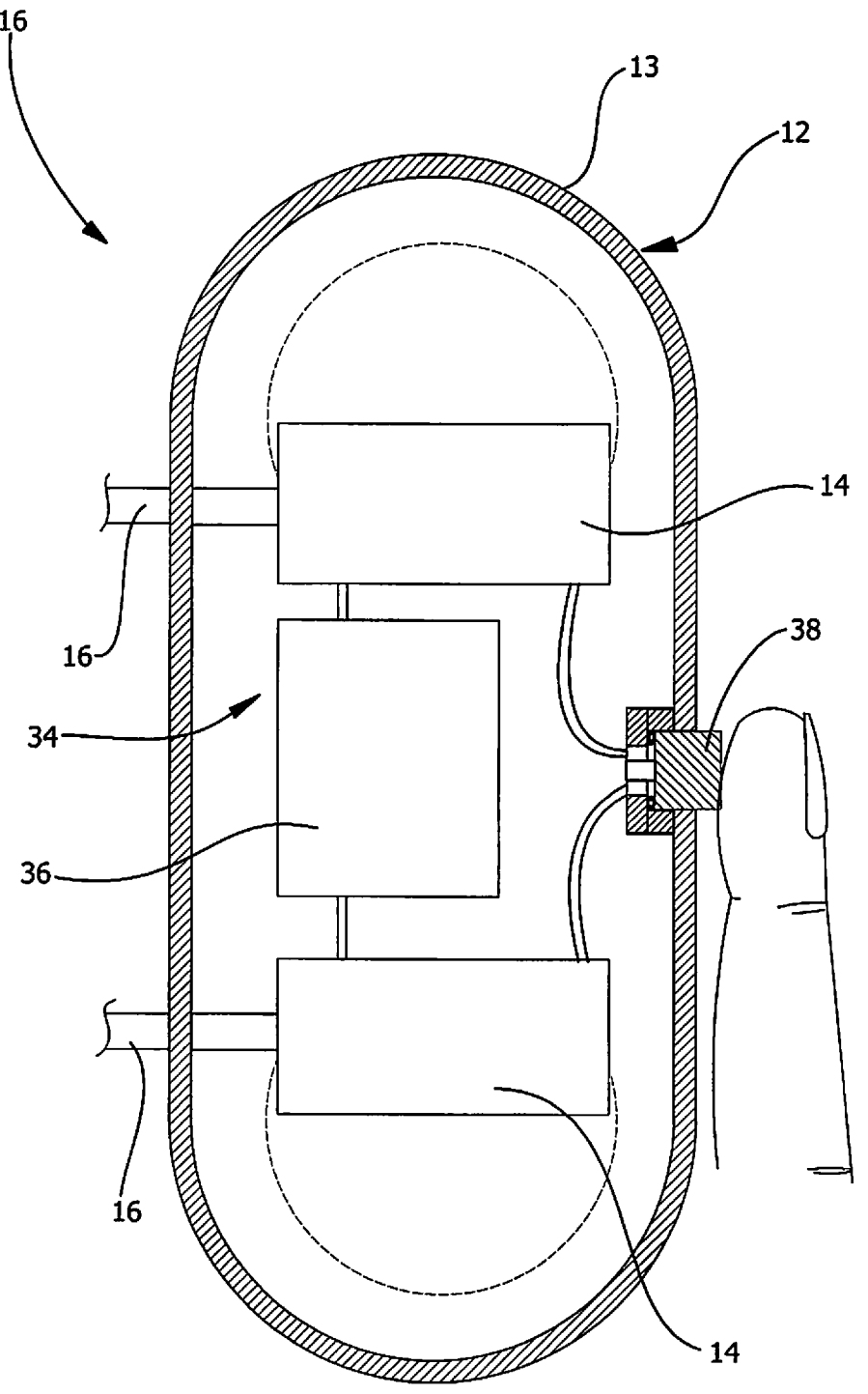
FIG. 6 is a cross section view of an embodiment of the disclosure taken from Arrows 6-6 in FIG. 4.
Figure 7:
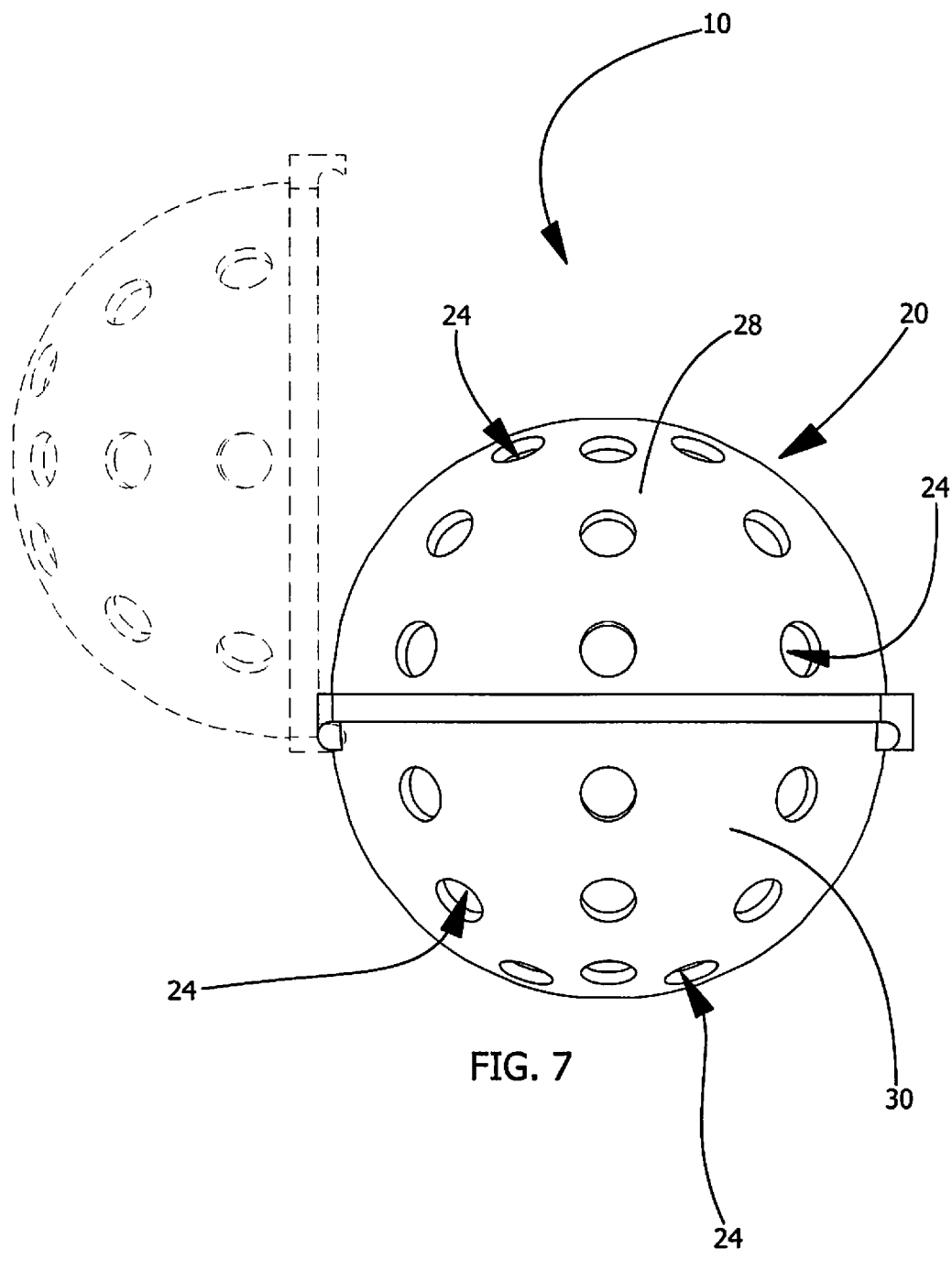
FIG. 7 is a detail view of a container of an embodiment of the disclosure.
Figure 8:
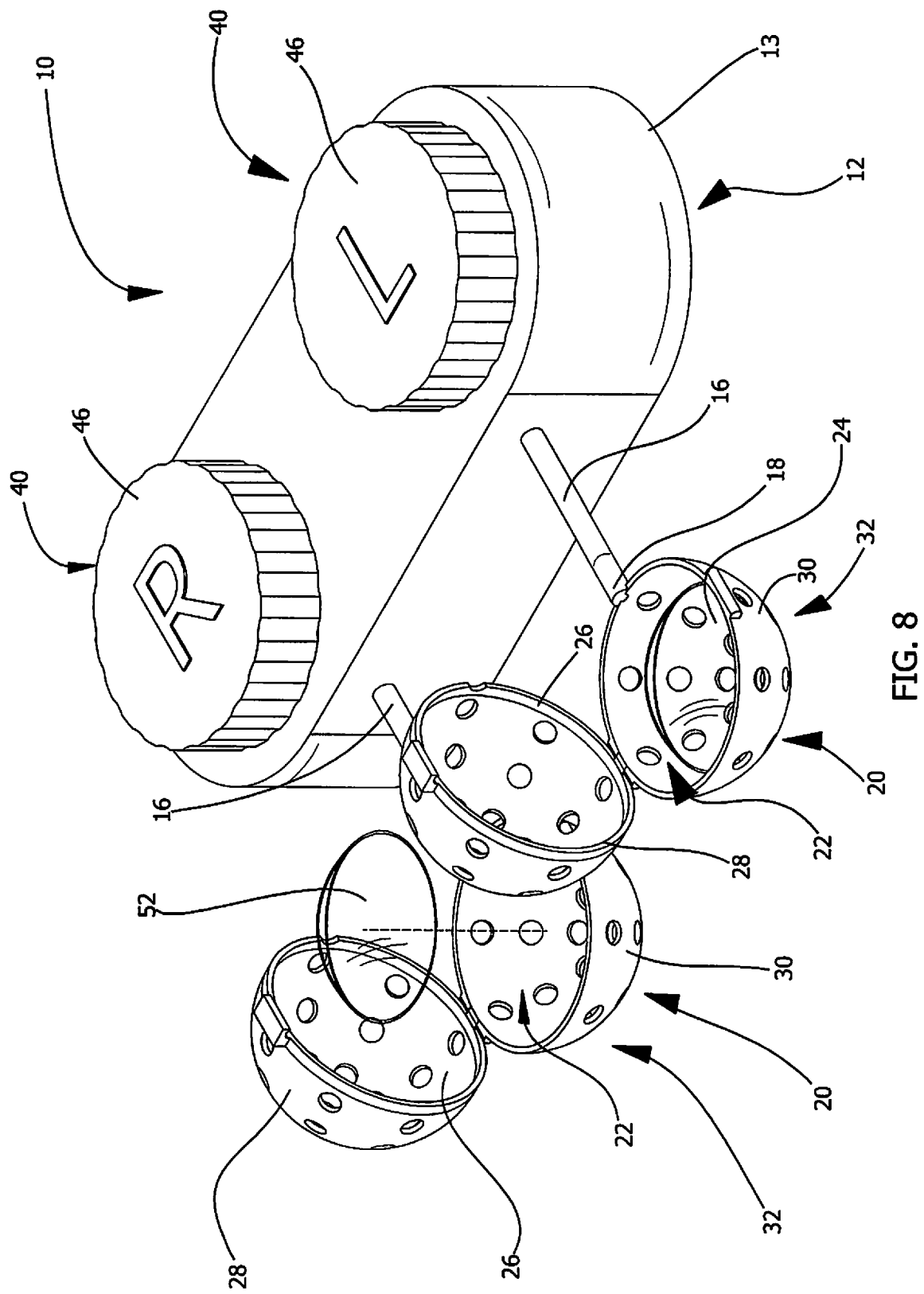
FIG. 8 is an in-use top front side perspective view of an embodiment of the disclosure.
Figure 9:
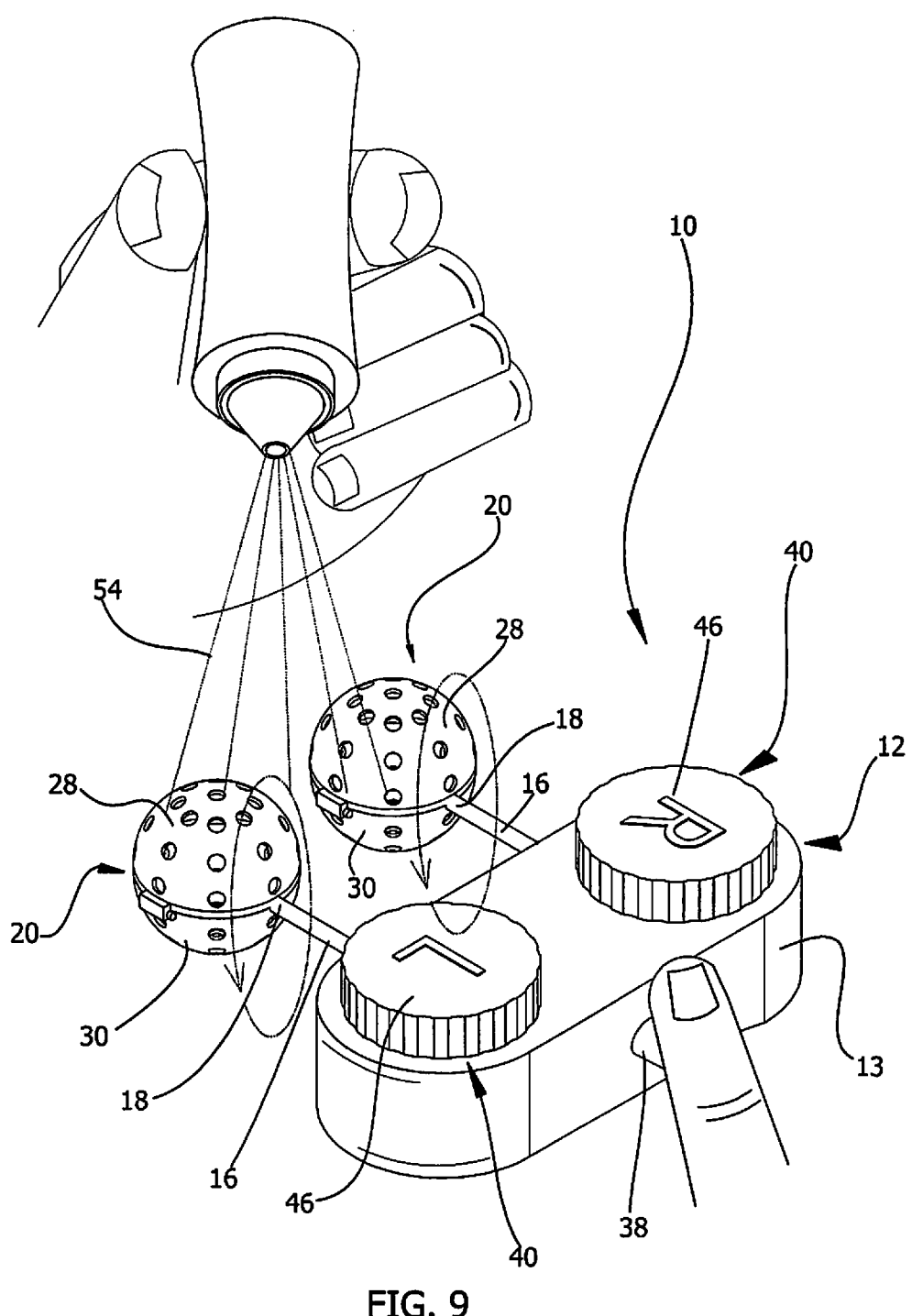
FIG. 9 is an in-use top rear side perspective view of an embodiment of the disclosure.

With reference now to the drawings, and in particular to FIGS. 1 through 8 thereof, a new contact lens cleaning apparatus embodying the principles and concepts of an embodiment of the disclosure and generally designated by the reference numeral 10 will be described.

As best illustrated in FIGS. 1 through 8, the contact lens cleaning apparatus 10 generally comprises a housing 12 and a pair of motors 14 mounted in the housing 12. Each one of a pair of shafts 16 is operatively coupled to an associated motor 14 of the pair of motors 14 and extends away from the associated motor 14 out of the housing 12. Each shaft 16 of the pair of shafts 16 is rotatable about a central axis of the shaft 16. Each one of a pair of containers 20 is mounted on a distal end 18 of an associated shaft 16 of the pair of shafts 16 with respect to the associated motor 14. Each container 20 defines an interior space 22 in the container 20 which has a size such that the container 20 is configured to contain an associated one of a pair of contact lenses 52. Each container 20 is urged to rotate by the associated shaft 16 when the associated shaft 16 rotates. Each container 20 of the pair of containers 20 is fluid permeable. Holes 24 extend into each container 20 which have a size such that the associated contact lens 52 cannot move through the hole 24. Each container 20 also has a spherical inner surface 26.

Each container 20 comprises a first segment 28 and a second segment 30 configured into a clamshell arrangement wherein the first segment 28 is pivotably coupled to the second segment 30. Each container 20 of the pair of containers 20 is positionable in an open configuration 32 wherein the first segment 28 is pivoted away from the second segment 30 to access the interior space 22. A power supply 34 is mounted in the housing 12 and is electrically coupled to the pair of motors 14. The power supply 34 comprises a battery 36. A power switch 38 is operatively coupled to the pair of motors 14 and is mounted on an exterior 13 of the housing 12.

A pair of storage vessels 40 is mounted on the exterior 13 of the housing 12. Each storage vessel 40 defines a storage space 42 in the storage vessel 40. The storage space 42 has a size such that the storage vessel 40 is configured to contain an associated contact lens 52 of the pair of contact lenses 52. Each storage vessel 40 has an open top 44, and a pair of caps 46 are provided for removably covering the open top 44 of each storage vessel 40. Each cap 46 of the pair of caps 46 is removably coupled to an associated storage vessel 40 via internal threads 48 which engage external threads 50 of the associated storage vessel 40. The storage vessels 40 are integrally formed with the housing 12.

In use, the contact lenses 52 are inserted individually into the associated containers 20, and the containers 20 are closed. The motors 14 are operated via the power switch 38 to urge the containers 20 to rotate, and a lens cleaning solution 54 is poured over the containers 20. The lens cleaning solution 54 enters the containers 20 via the holes 24 to rinse the contact lenses 52, and the containers 20 distribute the lens cleaning solution 54 across the contact lenses 52. The spherical inner surface 26 of the containers 20 facilitates a smooth movement of the containers 20 with respect to the contact lenses 52 such that the containers 20 do not damage the contact lenses 52. The lens cleaning solution 54 then drains through the holes 24 of the containers 20. The contact lenses 52 may also be stored in the storage vessels 40.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A contact lens cleaning apparatus comprising:
a housing;
a pair of motors being mounted in the housing;
a pair of shafts, each shaft of the pair of shafts being operatively coupled to an associated motor of the pair of motors, each shaft of the pair of shafts extending away from the associated motor and out of the housing, each shaft of the pair of shafts being rotatable about a central axis of the shaft;
a pair of containers, each container of the pair of containers being mounted on a distal end of an associated shaft of the pair of shafts with respect to the associated motor, each container of the pair of containers defining an interior space in the container, the interior space of each container of the pair of containers having a size such that the container is configured to contain an associated one of a pair of contact lenses, each container of the pair of containers being urged to rotate by the associated shaft when the associated shaft rotates, each container of the pair of containers being fluid permeable; and
a pair of storage vessels being mounted on the exterior of the housing, each storage vessel of the pair of storage vessels defining a separate storage space in the storage vessel, the storage space of each storage vessel of the pair of storage vessels having a size and shape such that the storage vessel is configured to contain an associated single contact lens of the pair of contact lenses.

2. The apparatus of claim 1, wherein each container of the pair of containers has a plurality of holes extending into the container, each hole of the plurality of holes having a size such that the associated contact lens cannot move through the hole.

3. The apparatus of claim 1, wherein each container of the pair of containers comprises a first segment and a second segment, the first segment and the second segment defining a clamshell arrangement wherein the first segment is pivotably coupled to the second segment, each container of the pair of containers being positionable in an open configuration wherein the first segment is pivoted away from the second segment to access the interior space.

4. The apparatus of claim 1, further comprising a power supply being mounted in the housing and being electrically coupled to the pair of motors.

5. The apparatus of claim 4, wherein the power supply comprises a battery.

6. The apparatus of claim 1, further comprising a power switch being operatively coupled to the pair of motors, the power switch being mounted on an exterior of the housing.

7. The apparatus of claim 1, wherein each storage vessel of the pair of storage vessels has an open top, further comprising a pair of caps, each cap of the pair of caps being removably coupled to an associated storage vessel of the pair of storage vessels to close the open top of the associated storage vessel.

8. The apparatus of claim 7, wherein each cap of the pair of caps has internal threads which engage external threads of the associated storage vessel.

9. The apparatus of claim 1, wherein the pair of storage vessels is integrally formed with the housing.

10. A contact lens cleaning apparatus comprising:
a housing;
a pair of motors being mounted in the housing;
a pair of shafts, each shaft of the pair of shafts being operatively coupled to an associated motor of the pair of motors, each shaft of the pair of shafts extending away from the associated motor and out of the housing, each shaft of the pair of shafts being rotatable about a central axis of the shaft;
a pair of containers, each container of the pair of containers being mounted on a distal end of an associated shaft of the pair of shafts with respect to the associated motor, each container of the pair of containers defining an interior space in the container, the interior space of each container of the pair of containers having a size such that the container is configured to contain an associated one of a pair of contact lenses, each container of the pair of containers being urged to rotate by the associated shaft when the associated shaft rotates, each container of the pair of containers being fluid permeable, each container of the pair of containers having a plurality of holes extending into the container, each hole of the plurality of holes having a size such that the associated contact lens cannot move through the hole, each container of the pair of containers comprising a first segment and a second segment, the first segment and the second segment defining a clamshell arrangement wherein the first segment is pivotably coupled to the second segment, each container of the pair of containers being positionable in an open configuration wherein the first segment is pivoted away from the second segment to access the interior space;

a power supply being mounted in the housing and being electrically coupled to the pair of motors, the power supply comprising a battery;

a power switch being operatively coupled to the pair of motors, the power switch being mounted on an exterior of the housing;

a pair of storage vessels being mounted on the exterior of the housing, each storage vessel of the pair of storage vessels defining a separate storage space in the storage vessel, the storage space of each storage vessel of the pair of storage vessels having a size and shape such that the storage vessel is configured to contain an associated single contact lens of the pair of contact lenses, each storage vessel of the pair of storage vessels having an open top, the pair of storage vessels being integrally formed with the housing; and a pair of caps, each cap of the pair of caps being removably coupled to an associated storage vessel of the pair of storage vessels to close the open top of the associated storage vessel, each cap of the pair of caps having internal threads which engage external threads of the associated storage vessel.

* * * * *